(12) United States Patent
Koenemann

(10) Patent No.: US 7,993,407 B2
(45) Date of Patent: Aug. 9, 2011

(54) ORTHOPAEDIC PROSTHESIS HAVING A POSITIONABLE STEM

(75) Inventor: Jeffery L. Koenemann, Plymouth, IN (US)

(73) Assignee: DePuy Products, Inc., Warsaw, IN (US)

( * ) Notice: Subject to any disclaimer, the term of this patent is extended or adjusted under 35 U.S.C. 154(b) by 917 days.

(21) Appl. No.: 11/771,216

(22) Filed: Jun. 29, 2007

(65) Prior Publication Data

US 2009/0005875 A1 Jan. 1, 2009

(51) Int. Cl.
*A61F 2/28* (2006.01)

(52) U.S. Cl. ............... 623/20.35; 623/20.36; 623/20.14; 623/20.15; 623/20.28; 623/20.29

(58) Field of Classification Search .... 623/23.15–23.38, 623/20.14, 20.15, 20.28, 20.29, 20.35, 20.36, 623/22.4–23.9; *A61F 2/38*
See application file for complete search history.

(56) References Cited

U.S. PATENT DOCUMENTS

| | | | |
|---|---|---|---|
| 5,152,796 A | | 10/1992 | Slamin |
| 6,071,311 A | * | 6/2000 | O'Neil et al. ............... 623/20.15 |
| 6,171,342 B1 | | 1/2001 | O'Neil et al. |
| 2006/0030945 A1 | | 2/2006 | Wright |
| 2006/0173547 A1 | * | 8/2006 | Ensign ....................... 623/20.15 |

FOREIGN PATENT DOCUMENTS

| | | |
|---|---|---|
| EP | 0781535 | 7/1997 |
| EP | 0820739 | 1/1998 |
| EP | 0980679 | 2/2000 |
| EP | 1430856 | 6/2004 |

OTHER PUBLICATIONS

European Search Report for European Patent Application No. 08158894.9-2310, Sep. 15, 2008, 7 pgs.
DePuy Orthopaedics, Inc., "The P.F.C. Sigma Femoral Adapter Surgical Technique", 2006, 32 pages.
DePuy Orthopaedics, Inc., "Surgical Technique for Use with P.F.C. Sigma Knee Systems: Primary Cruciate-Retaining Cruciate-Substituting Procedure", 2998, 108 pages.

* cited by examiner

*Primary Examiner* — David Isabella
*Assistant Examiner* — Jason-Dennis Stewart
(74) *Attorney, Agent, or Firm* — Barnes & Thornburg LLP

(57) ABSTRACT

An orthopaedic prosthesis includes a femoral component configured to be coupled to a surgically-prepared surface of the distal end of a femur and a plate having an aperture defined therein. The plate is configured to be coupled to the femoral component in one of a number of orientations such that the location of the aperture is adjustable based on the orientation of the plate. The orthopaedic prosthesis also includes a stem configured to be coupled to the femoral component via a bolt. The position of the stem relative to the femoral component is adjustable based on the orientation of the plate.

17 Claims, 12 Drawing Sheets

ORTHOPAEDIC PROSTHESIS HAVING A POSITIONABLE STEM

TECHNICAL FIELD

The present disclosure relates generally to orthopaedic prostheses, and particularly to a femoral joint prostheses for a knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. The femoral component generally includes a pair of spaced apart condylar portions, the surfaces of which articulate with corresponding surfaces of the polymer bearing. The femoral component may include a stem or post that is implanted into the intramedullary canal of the distal end of the femur to provide stability. In some applications, a stem extension may be coupled to the femoral component to increase the overall length of the stem of the femoral component.

SUMMARY

According to one aspect, an orthopaedic prosthesis may include a femoral component and a plate. The femoral component may be configured to be coupled to a surgically-prepared surface of the distal end of a femur. Additionally, the femoral component may include a pair of spaced apart condyles and an opening defined therebetween. The opening of the femoral component may be defined, for example, by an anterior sidewall, a posterior sidewall, a medial sidewall, and a lateral sidewall. In some embodiments, each of the medial and lateral sidewalls of the femoral component may include a slot defined therein. Additionally, in some embodiments, the slots defined in the medial and lateral sidewalls may be centrally located along medial and lateral sidewalls.

The plate of the orthopaedic prosthesis may include an aperture defined therethrough. The plate may be configured to be coupled to the femoral component in one of a number of orientations such the aperture is in registry with the opening of the femoral component and the location of the aperture is adjustable relative to the femoral component based on the orientation. In embodiments wherein the femoral component includes a number of slots, the plate may include a number of corresponding tabs configured to be received in the slots of the medial and lateral sidewalls when the plate is coupled to the femoral component. In some embodiments, the aperture of the plate may be longitudinally offset relative to the center of the plate. For example, the aperture of the plate may be longitudinally offset relative to the center of the plate by a distance of about 1 millimeter to about 6 millimeters. In particular, the aperture of the plate may be longitudinally offset relative to the center of the plate by a distance of about 2 millimeters or 4 millimeters. In other embodiments, the aperture may be centrally located in the plate.

In some embodiments, the plate may include a body and a flange defined on a distal side of the body. In such embodiments, the body of the plate is received in the opening of the femoral component when the plate is coupled thereto. The plate may be configured to be coupled to the femoral component in one of a first orientation and a second orientation. In such embodiments, the plate may be configured such that the aperture of the plate is offset in an anterior direction relative to the center of the opening when the plate is in the first orientation and offset in a posterior direction relative to the center of the opening when the plate is in the second orientation. In some embodiments, the femoral component may include indicia from which the location of the aperture may be determined. In other embodiments, the orthopaedic prosthesis may include a stem having a threaded aperture and a bolt. The bolt may be configured to be inserted through the aperture of the plate and into the threaded aperture of the stem to secure the stem to the femoral component. In such embodiments, the stem may be configured to be coupled to the femoral component in one of a number of locations based on the orientation of the plate.

According to another aspect, an orthopaedic prosthesis may include a femoral component configured to be coupled to a surgically-prepared surface of the distal end of a femur and a plate configured to be coupled to the femoral component. The femoral component may include an opening for facilitating the attachment of a stem to the femoral component. The opening of the femoral component may be defined, for example, by an anterior sidewall, a posterior sidewall, a medial sidewall, and a lateral sidewall. In some embodiments, each of the medial and lateral sidewalls of the femoral component may include a slot defined therein. In such embodiments, the plate may include a number of tabs configured to be received in the slots of the medial and lateral sidewalls when the plate is coupled to the femoral component.

The plate of the orthopaedic prosthesis may include a body and a flange defined on a distal side of the body. The plate may also include an aperture defined therethrough. The plate may be configured to be coupled to the femoral component in one of a number of orientations such that the body of the plate is received in the opening and the location of the aperture relative to the femoral component is determined based on the orientation of the plate. The aperture of the plate may be longitudinally offset relative to the center of the plate. Alternatively, the aperture may be centrally located in the plate. The flange of the plate may be configured to contact a distal surface of the femoral component when the base of the plate is received in the opening of the femoral component.

Additionally, the plate may be configured to be coupled to the femoral component in one of a first orientation and a second orientation. The aperture of the plate may be offset in an anterior direction relative to the center of the opening when the plate is in the first orientation and offset in a posterior direction relative to the center of the opening when the plate is in the second orientation. In some embodiments, the orthopaedic prosthesis may include a stem having a threaded aperture and a bolt. The bolt may be configured to be inserted through the aperture of the plate and into the threaded aperture of the stem to secure the stem to the femoral component. In such embodiments, the stem may be configured to be coupled to the femoral component in one of a number of locations based on the orientation of the plate. In such embodiments, the femoral component and the stem may include indicia from which the location of the aperture may be determined.

According to yet another aspect, an orthopaedic prosthesis assembly may include a femoral component and a plate configured to be coupled to the femoral component. The femoral component may be configured to be coupled to a surgically-prepared surface of the distal end of a femur. Additionally, the femoral component may include a pair of spaced apart condyles and an opening defined therebetween. The plate may include a body and a flange defined on a distal side of the body. The plate may have an aperture defined therethrough. The plate may be configured to be coupled to the femoral component in a first orientation and a second orientation such that the body of the plate is received in the opening, the aperture is offset in the anterior direction when the plate is in the first orientation, and the aperture is offset in the posterior direction when the plate is in the second orientation. The orthopaedic prosthesis assembly may also include a stem having a threaded aperture and a bolt. The bolt may be configured to be inserted through the aperture of the plate and into the threaded aperture of the stem to secure the stem to the femoral component in one of a number of locations based on the orientation of the plate.

BRIEF DESCRIPTION OF THE DRAWINGS

The detailed description particularly refers to the following figures, in which.

DETAILED DESCRIPTION OF THE DRAWINGS

Figure 1:
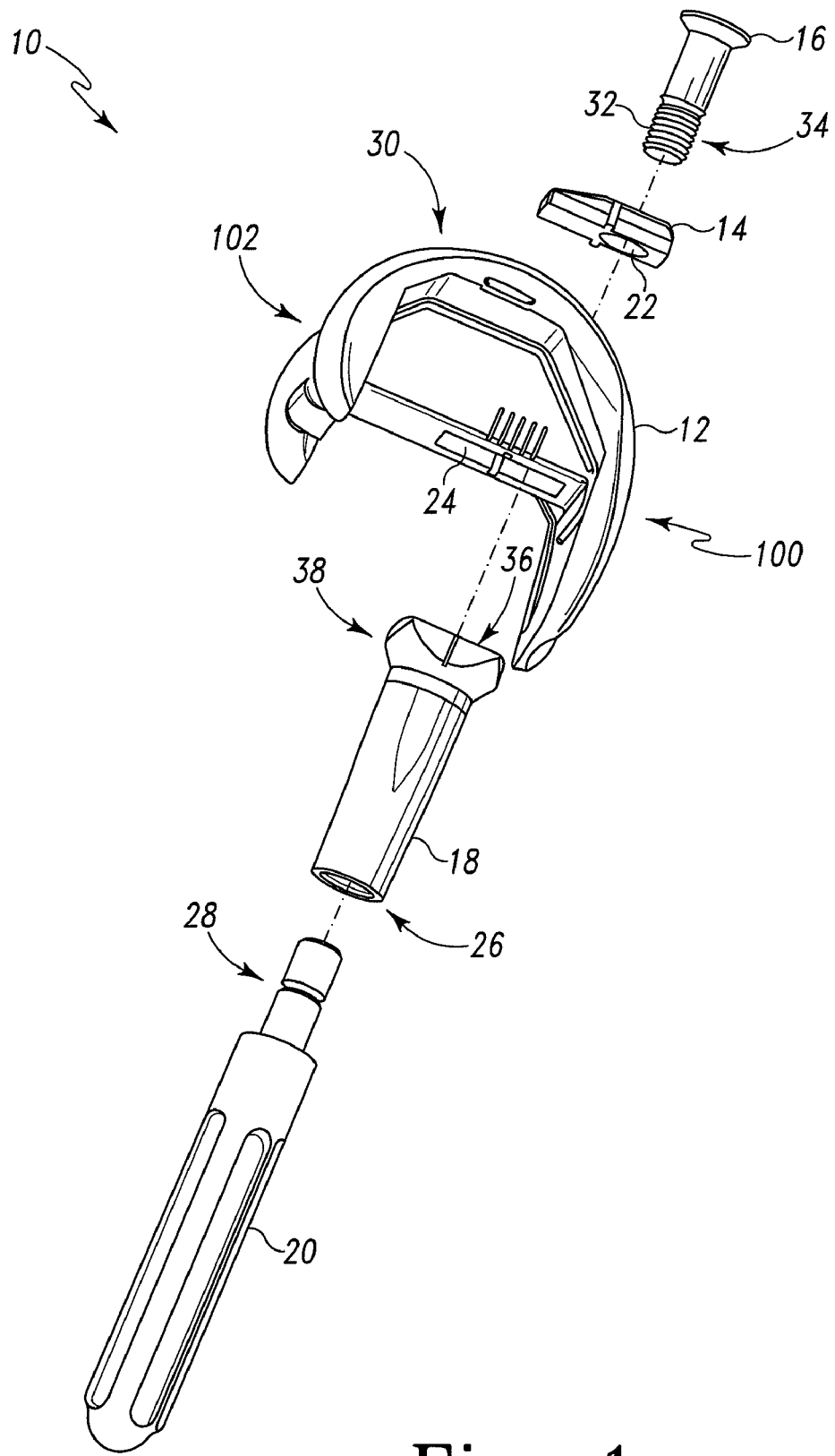
FIG. 1 is an exploded perspective view of one embodiment of an orthopaedic prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Figure 2:
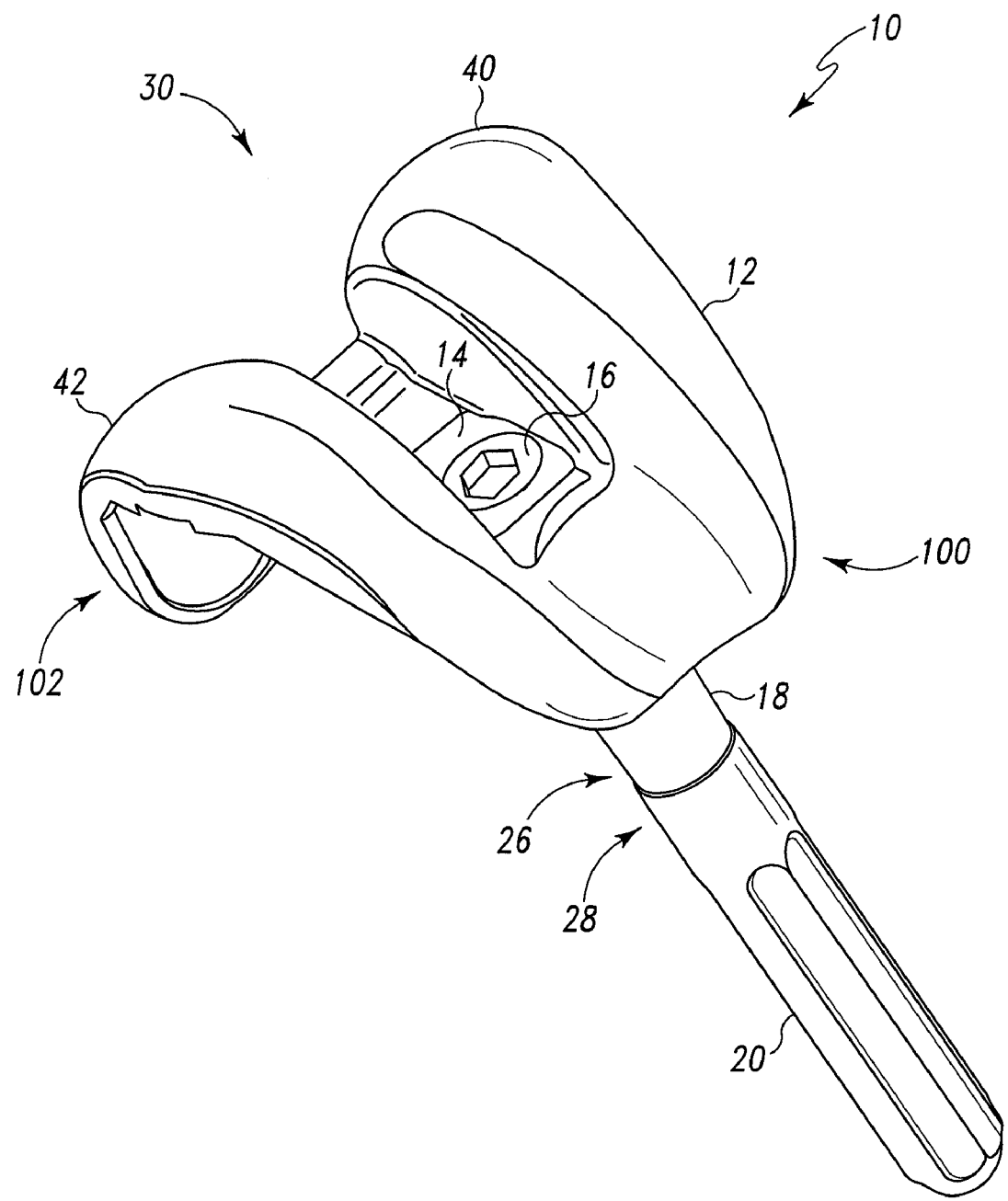
FIG. 2 is a perspective view of the orthopaedic prosthesis of FIG. 1 in an assembled configuration.

Referring to FIGS. 1 and 2, an orthopaedic prosthesis 10 includes a femoral component 12, a mounting plate 14, a bolt 16, and a stem 18. The femoral component 12, plate 14, bolt 16, and stem 18 are configured to be coupled together as illustrated in FIG. 2. Additionally, in some embodiments, orthopaedic prosthesis 10 may include a stem extension 20.

The stem extension 20 is configured to be coupled to the stem 18 to increase thereby the overall length of the stem. The stem extension 20 may be coupled to the stem 18 via any suitable method and/or devices. For example, the stem extension 20 may be configured to be pressure-fitted to the stem 18 via a tapered joint or the like. Alternatively, the stem extension 20 and stem 18 may be configured to be attached via a threaded stud and a corresponding threaded bore. For example, the stem 18 may include a threaded bore (not shown) located at a proximal end 26 of the stem 18 and configured to receive a threaded stud (not shown) located at a distal end 28 of the stem extension 20. Alternatively, the stem 18 may include a threaded stud at the proximal end 26, which is threaded or screwed into a threaded bore located at the distal end 28 of the stem extension 20. In other embodiments, other methods, devices, and/or features may be used to couple the stem extension 20 to the stem 18 such as, for example, adhesives, detents, twist-locks, and/or the like The stem 18 is configured to be coupled to the femoral component 10 via use of the bolt 16 and the plate 14. To do so, the plate 14 is coupled to the femoral component 10 on a distal side 30 of the component 10. As discussed in more detail below in regard to FIGS. 5 and 6, when the plate 14 is coupled to the femoral component 10, a portion of the plate 14 is received in an opening 22 defined in the femoral component 10.

Once the plate 14 is coupled to the femoral component 10, the bolt 16 is inserted through an aperture 22 of the plate 14, which is sized to receive the bolt 16. As such, the bolt 16 extends through the aperture 22 of the plate 14 and the opening 22 of the femoral component 10. The bolt 16 includes a threaded portion 32 defined at a proximal end 34. The threaded portion 32 of the bolt 16 is received by a threaded bored 36 of the stem 18, which is located at the distal end 38 of the stem 18. The bolt 16 is secured to the stem 18 by threading or screwing the threaded portion 32 of the bolt into the threaded bore 36 of the stem 18. As discussed in more detail below, the location at which the stem 18 is secured to the femoral component 10 is determined based on and adjustable by selection of the type of plate 14 and the orientation of the plate 14 relative to the femoral component 10. For example, the stem 18 may be secured to the femoral component 10 in a neutral or centered location or a location that is offset from the centered location.

Figure 3:
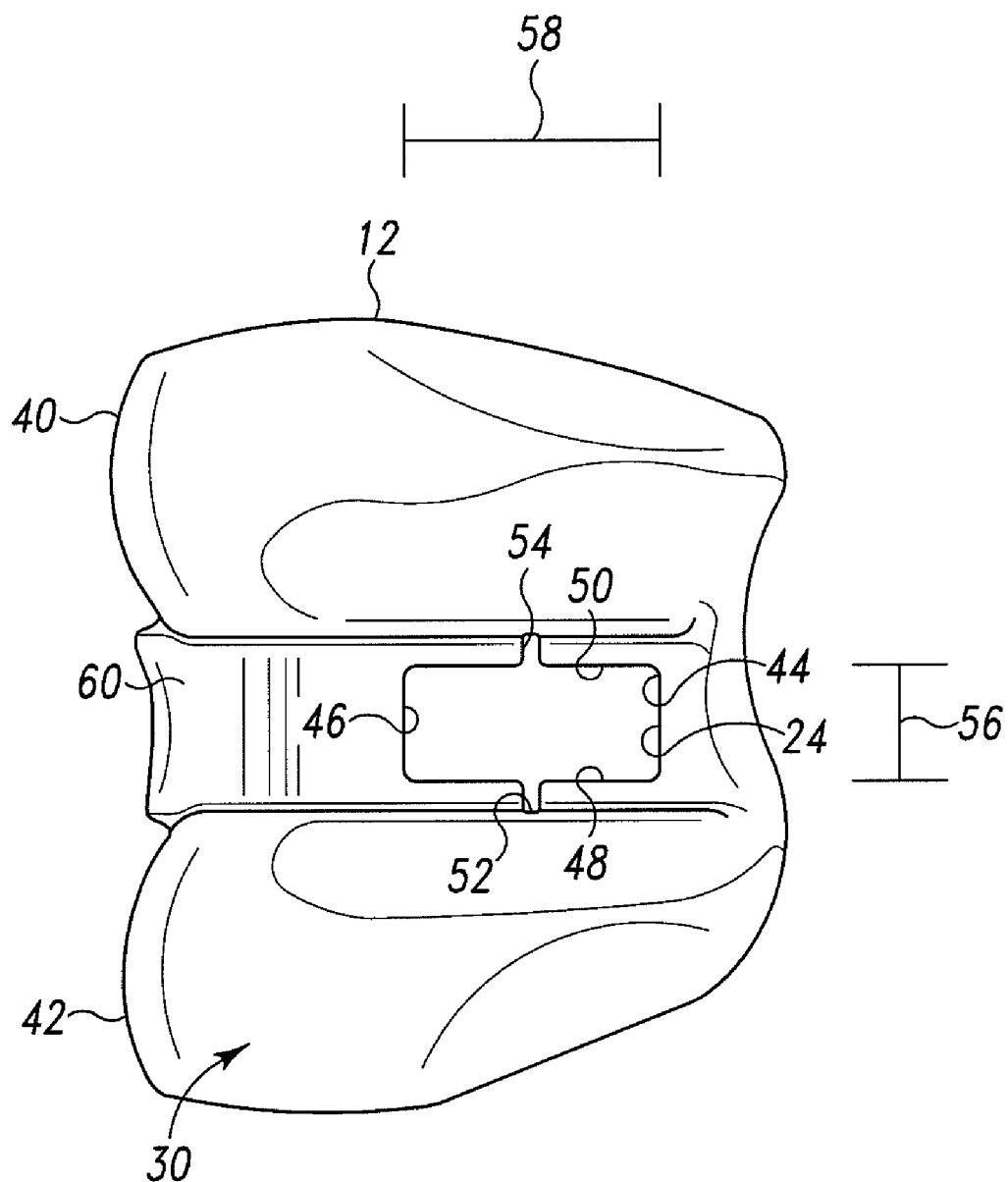
FIG. 3 is a top plan view of a femoral component of the orthopaedic prosthesis of FIG. 1.
Figure 4:
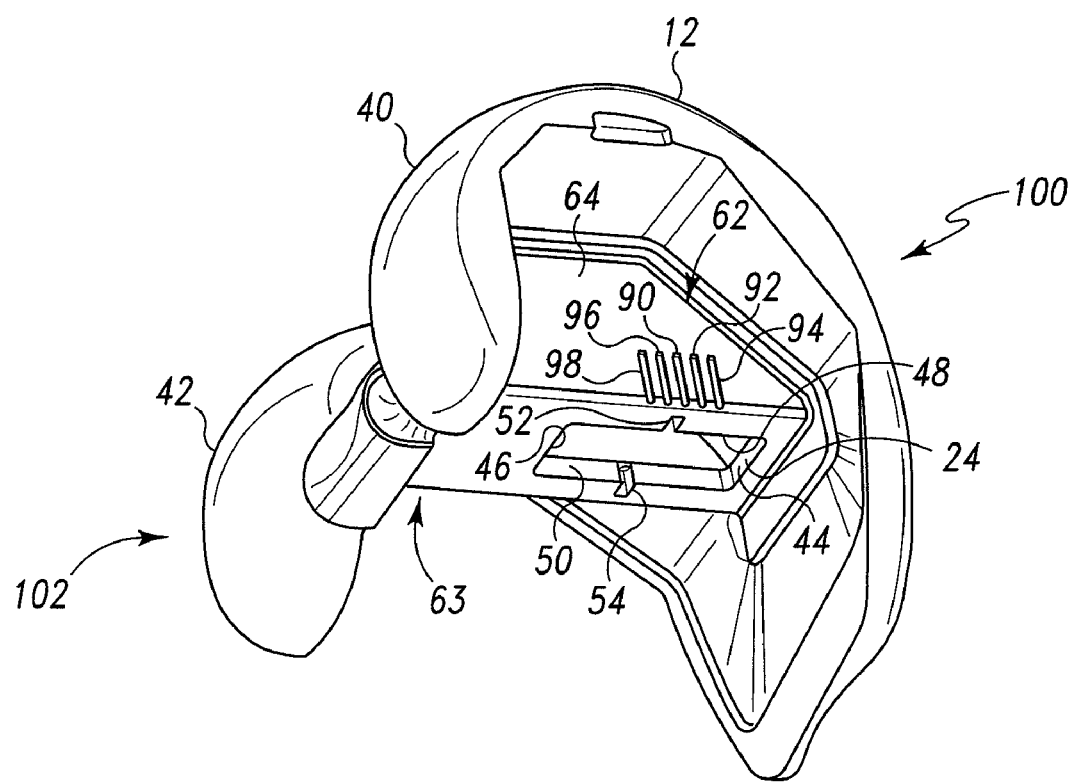
FIG. 4 is a bottom perspective view of the femoral component of FIG. 3.

Referring now to FIGS. 3-4, the femoral component 12 is configured to be coupled to a surgically-prepared surface of the distal end of a patient's femur (not shown). When the femoral component 12 is coupled to the patient's femur, the stem 18 (and stem extension 20) is embedded in the patient's bone. The femoral component 12 may be secured to the patient's femur via use of bone adhesive or other attachment means. The femoral component 12 includes a pair of condyles 40, 42. In use, the condyles 40, 42 replace the natural condyles of the patient's femur and are configured to articulate on the proximal end of the patient's natural or surgically-prepared tibia.

The femoral component includes a planar surface 60 defined between the condyles 40, 42. The opening 24 is defined in the planar surface 60. As illustrated in FIG. 3, the opening 24 is defined by an anterior sidewall 44, a posterior sidewall 46, a medial sidewall 48, and a lateral sidewall 50. The illustrative femoral component 10 is configured to be attached to a patient's right femur. However, it should be appreciated that the femoral component 10 may also be coupled to the patient's left femur. In such embodiments, the sidewall 48 would a laterally oriented sidewall while the sidewall 50 would be a medially oriented sidewall.

The sidewalls 48, 50 each include a slot 52, 54, respectively. The slots 52, 54 extend outwardly toward the medial and lateral sides of the femoral component 10. As discussed in more detail below in regard to FIGS. 5 and 6, the slots 52, 54 are configured to receive corresponding tabs 70, 72 of the plate 14 (see FIGS. 5 and 6) when the plate 14 is coupled to the femoral component 10. The slots 52, 54 are defined at a central location along the sidewalls 48, 50. Although the femoral component 10 includes two slots 52, 54 in the illustrative embodiments, the femoral component 10 may include any number of slots in other embodiments. For example, in some embodiments, the femoral component 10 may include multiple, evenly spaced slots, which may be defined in any of the sidewalls 44, 46, 48, 50.

As shown in FIG. 3, the opening 24, as defined by the sidewalls 44, 46, 48, and 50, has a substantially rectangular top profile. As discussed above in regard to FIGS. 1 and 2, the opening 24 of the femoral component 10 is configured to receive a portion of the plate 14 when the plate 14 is coupled to the component 10. As such, the opening 24 has suitable dimensions such that the bolt 16 is capable of extending therethrough. That is, the opening 24 has a width 56 and a length 58 greater than the diameter 74 (see FIG. 5) of the aperture 22 of the plate 14 such that the bolt 16 is capable of extending through the opening 24 of the femoral component 10. The width 56 of the opening 24 is equal to or slightly larger than the diameter 74 of the aperture 22 of the plate 14. The length 58 of the opening 24, however, is greater than the diameter 74 of the aperture 22 (i.e., greater than the diameter of the bolt 16). For example, in one particular embodiment, the opening 24 has a width 56 of about 0.400 inches and a length 58 of about 0.900 inches. As such, the bolt 16 is positionable in a number of locations in which the bolt 16 extends through the opening 24 of the femoral component 10. As discussed below in regard to FIGS. 5 and 6, the various positioning of the bolt 16 allows the stem 18 to be coupled to the femoral component 10 in one of a number of locations.

As illustrated in FIG. 4, in some embodiments, the femoral component 10 may include a number of marks or other indicia 62 configured to provide visual notification of the amount of offset of the aperture 22 of the plate 14, and thereby the amount of offset of the stem 18, to an orthopaedic surgeon or other healthcare provider as discussed in more detail below in regard to FIGS. 5-13. For example, in the illustrative embodiment, the femoral component 10 includes five offset marks including a center or no-offset mark and four offset marks. That is, the femoral component 10 includes a center or no-offset mark 90, a first anterior or positive offset mark 92, a second anterior or positive offset mark 94, a first posterior or negative offset mark 96, and a second posterior or negative offset mark 98. However, in other embodiments, the femoral component may include any number of offset marks or other indicia. The polarity of the marks 62 may be based on, for example, whether the mark is closer to the anterior side 100 or the posterior side 102 of the femoral component 10. The marks or indicia 62 are defined on one or more inner sidewalls 63, 64 of the femoral component 10.

Figure 5:
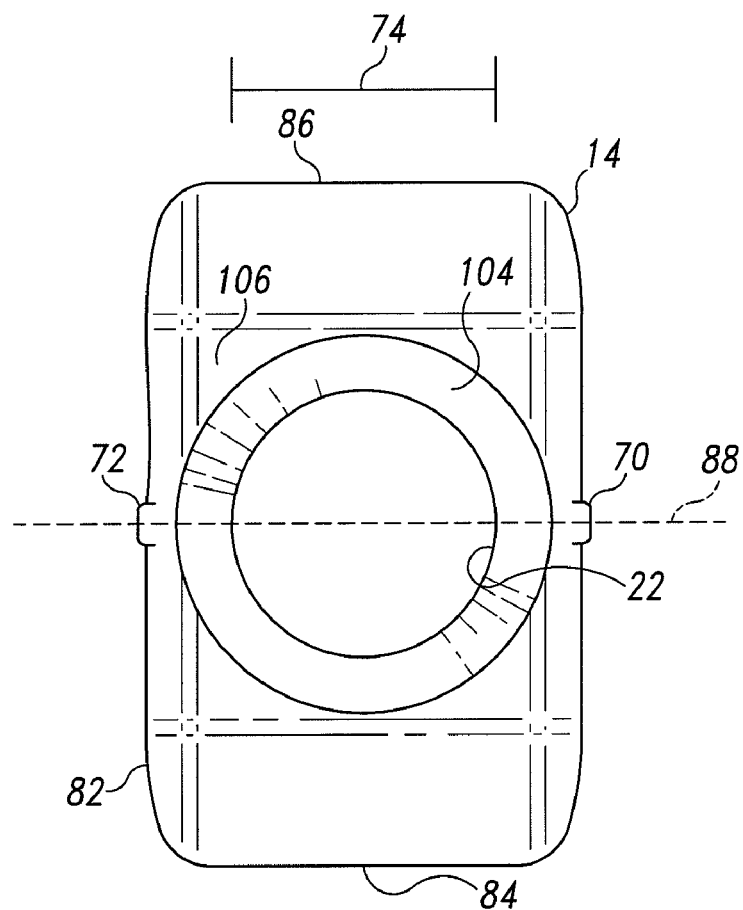
FIG. 5 is a top plan view of one embodiment of a plate of the orthopaedic prosthesis of FIG. 1.
Figure 6:
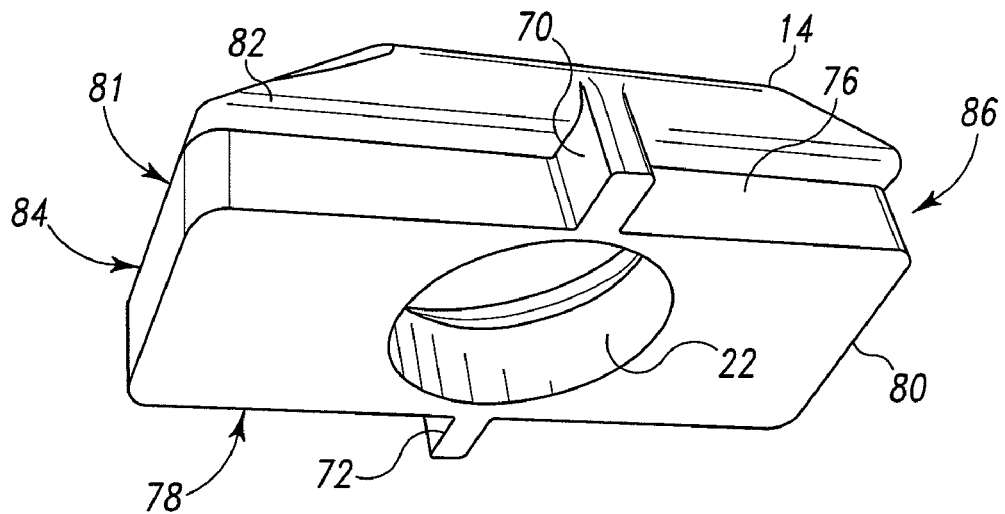
FIG. 6 is a bottom perspective view of the plate of FIG. 5.

Referring now to FIGS. 5 and 6, the plate 14 includes a body 80 and a flange 82 defined on a distal side 84 of the body 80. The body 80 of the plate 14 is configured to be received in the opening 24 of the femoral component 10 when the plate 14 is coupled thereto. As such, body 80 of the plate 14 has a length and width slightly smaller than the length 58 and width 56 of the opening 24. In addition, as discussed above in regard to FIGS. 3-4, the plate 14 includes a number of tabs or protrusions 70, 72, which extend from the sidewalls 76, 78 of the body 80. The tabs 70, 72 are located on the plate 14 such that when the plate 14 is coupled to the femoral component 10, the tabs 70, 72 are received in the slots 52, 54 defined in the femoral component 10. Because the slots 52, 54 are centrally defined in the sidewalls 48, 50 that define the opening 24, the illustrative plate 14 may be positioned in one of two orientations such that tabs 70, 72 are received in the slots 52, 54. For example, the plate 14 may be coupled to the femoral component 10 in one orientation such that a first end 84 of the plate 14 is positioned toward the anterior side 100 of the femoral component 10 and a second end 86 of the plate 14 is positioned toward the posterior side 102 of the femoral component 10. Alternatively, the plate 14 may be rotated 180 degrees and coupled to the femoral component 10 in a second orientation such that the first end 84 of the plate 14 is positioned toward the posterior side 102 of the femoral component 10 and the second end 86 of the plate 14 is positioned toward the anterior side 100 of the femoral component 10.

As discussed previously, the aperture 22 of the plate 14 is configured to receive the bolt 16. As such, the aperture 22 may be defined in the plate 14 such that the diameter 74 of the aperture 22 is slightly larger than the diameter of the bolt 16. In some embodiments, as illustrated in FIG. 5, a portion 104 of the top surface 106 of the plate 14 may be beveled inwardly toward the aperture 22 to allow the bolt 16 to be properly seated on the plate 14. The aperture 22 may be defined in the plate 14 in any one of a number of different locations. For example, in the embodiment illustrated in FIGS. 5 and 6, the aperture 22 is defined in the plate 14 in a central location. That is, the aperture 22 is defined in the plate 14 such that the center of the aperture 22 is aligned with the longitudinal center of the plate 14 as indicated in FIG. 5 by axis line 88.

Figure 7:
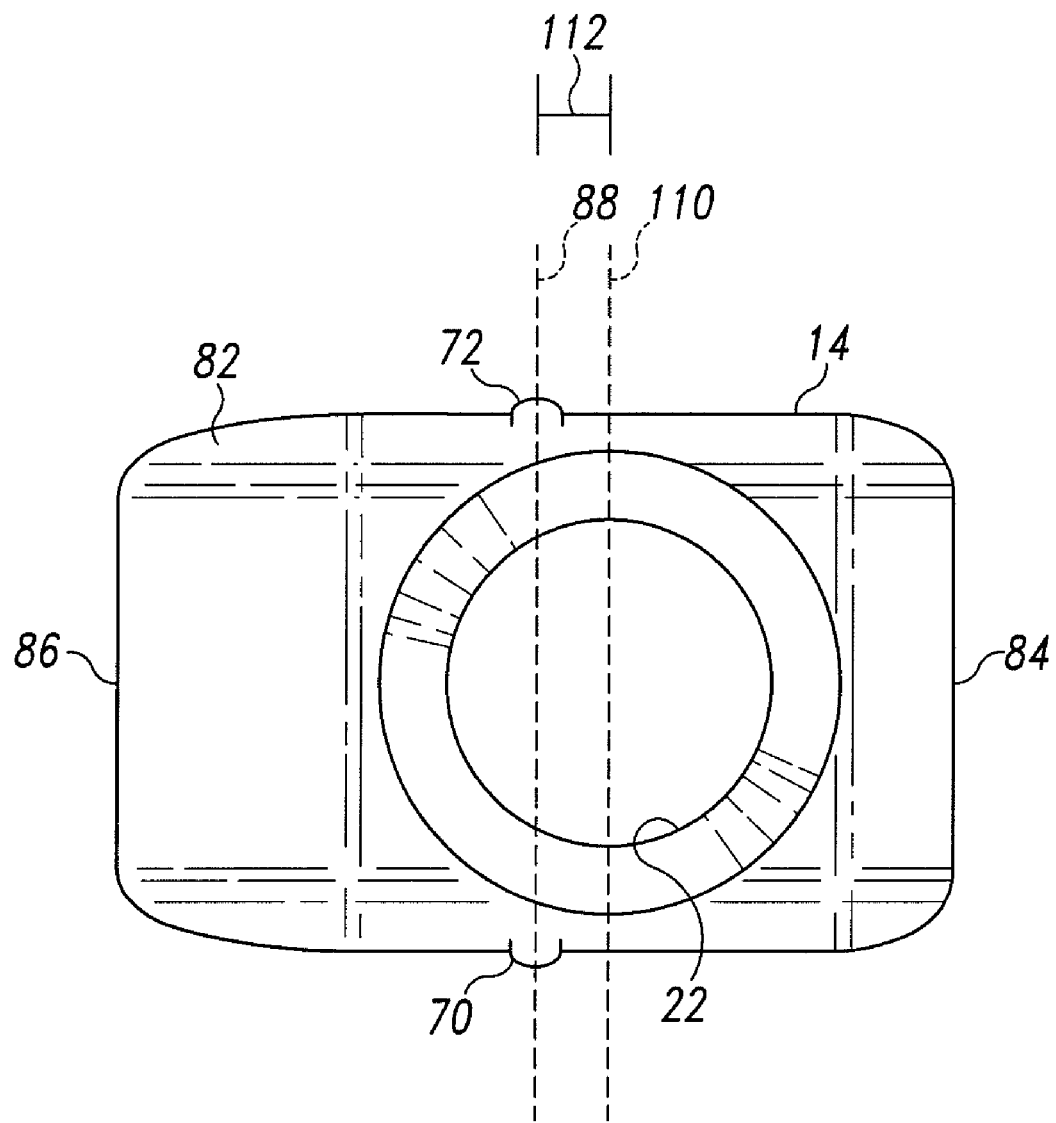
FIG. 7 is a top plan view of another embodiment of the plate of the orthopaedic prosthesis of FIG. 1.
Figure 8:
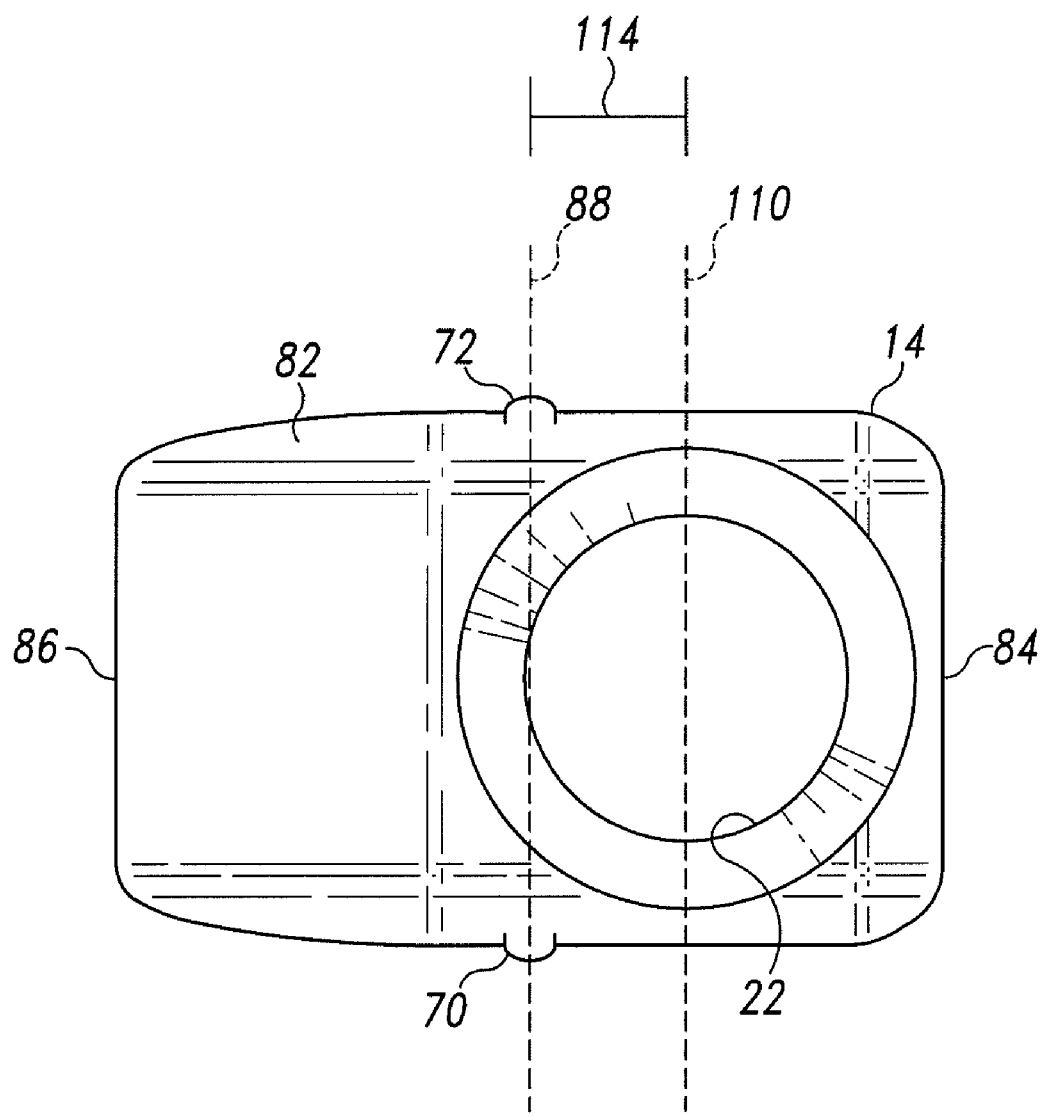
FIG. 8 is a top plan view of another embodiment of the plate of the orthopaedic prosthesis of FIG. 1.

In other embodiments, the aperture 22 may be defined in the plate 14 in an offset location. For example, in one embodiment as illustrated in FIG. 7, the aperture 22 is defined in the plate 14 in a location offset from the center of the plate 14. That is, the aperture 22 is defined in the plate 14 such that the center of the aperture 22, as indicated in FIG. 7 by axis line 110, is offset from the longitudinal center of the plate 14, as indicated in FIG. 7 by axis line 88, a distance 112. The aperture 22 may be offset from the center of the plate 14 any distance. For example, in the illustrative embodiment of FIG. 7, the aperture 22 is offset from the center of the plate 14 a distance of about two millimeters (i.e., the distance 112 is equal to about two millimeters). However, in other embodiments, the aperture 22 may be offset from the center of the plate 14 greater or less than two millimeters. For example, in the illustrative embodiment of FIG. 8, the aperture 22 is defined in the plate 14 such that the center of the aperture 22, as indicated in FIG. 8 by axis line 110, is offset from the longitudinal center of the plate 14, as indicated in FIG. 8 by axis line 88, a distance 114 equal to about four millimeters. As such, it should be appreciated that the aperture 22 may be defined in the plate 14 in a central location or in a location offset from the center of the plate 14.

In embodiments wherein the aperture 22 is defined in the plate 14 in an offset location, the position of the aperture 22 relative to the femoral component 10 is determined based on the orientation in which the plate 14 is coupled to the femoral component 10. For example, if the aperture 22 is offset from the center of the plate 14 toward the first end 84 of the plate 14 (see, e.g., FIG. 7) and the plate 14 is coupled to the femoral component 10 in an orientation such that the first end 84 of the plate 14 is positioned toward the anterior side 100 of the femoral component 10. In such case, the aperture 22 is similarly positioned or offset toward the anterior side 100 of the femoral component 10. That is, the plate 14 is coupled to the femoral component 10 such that the aperture 22 is offset in an anterior direction relative to the femoral component 10. Conversely, the plate 14 may be rotated 180 degrees and coupled to the femoral component 10 in an orientation such that the first end 84 of the plate 14 is positioned toward the posterior side 102 of the femoral component 10, the aperture 22 is similarly positioned or offset toward the posterior side 102 of the femoral component 10. That is, the plate 14 is coupled to the femoral component 10 such that the aperture 22 is offset in a posterior direction relative to the femoral component 10. As such, it should be appreciated that a single plate 14 having an offset aperture 2 defined therein may be used to provide a positive offset (e.g., an anterior offset) or a negative offset (e.g., a posterior offset) based on the orientation in which the plate 14 is coupled to the femoral component 10.

Referring now to FIGS. 9-13, prior to implantation into the patient, the components of the orthopaedic prosthesis 10 are coupled together. To do so, the plate 14 is initially coupled to the femoral component 10. As discussed above, the plate 14 may be coupled to the femoral component 10 in one of a number of orientations. Because the slots 52, 54 defined in the femoral component 10 and the tabs 70, 72 of the plate 14 are centrally located in the illustrative embodiment, the plate 14 may be coupled to the femoral component 10 in an orientation such that the first end 84 of the plate 14 is positioned toward the anterior side 100 of the femoral component 10. Alternatively, the plate 14 may be rotated 180 degrees and positioned in another orientation such that the first end 84 of the plate 14 is positioned toward the posterior side 102 of the femoral component 10. The plate 14 may be coupled to the femoral component 10 by positioning the plate 14 such that the body 80 of the plate is received in the opening 24 of the femoral component 10. When so positioned, the tabs 70, 72 of the plate 14 are received in the slots 52, 54 defined in the femoral component 10. Additionally, because the flange 82 of the plate 14 has a width greater than the width 56 of the opening 24, the flange 82 of the plate 14 contacts the planar surface 60 defined between the condyles 40, 42 when the plate 14 is coupled to the femoral component 10. In this way, the plate 14 is prevented from passing completely through the opening 24.

Figure 9:
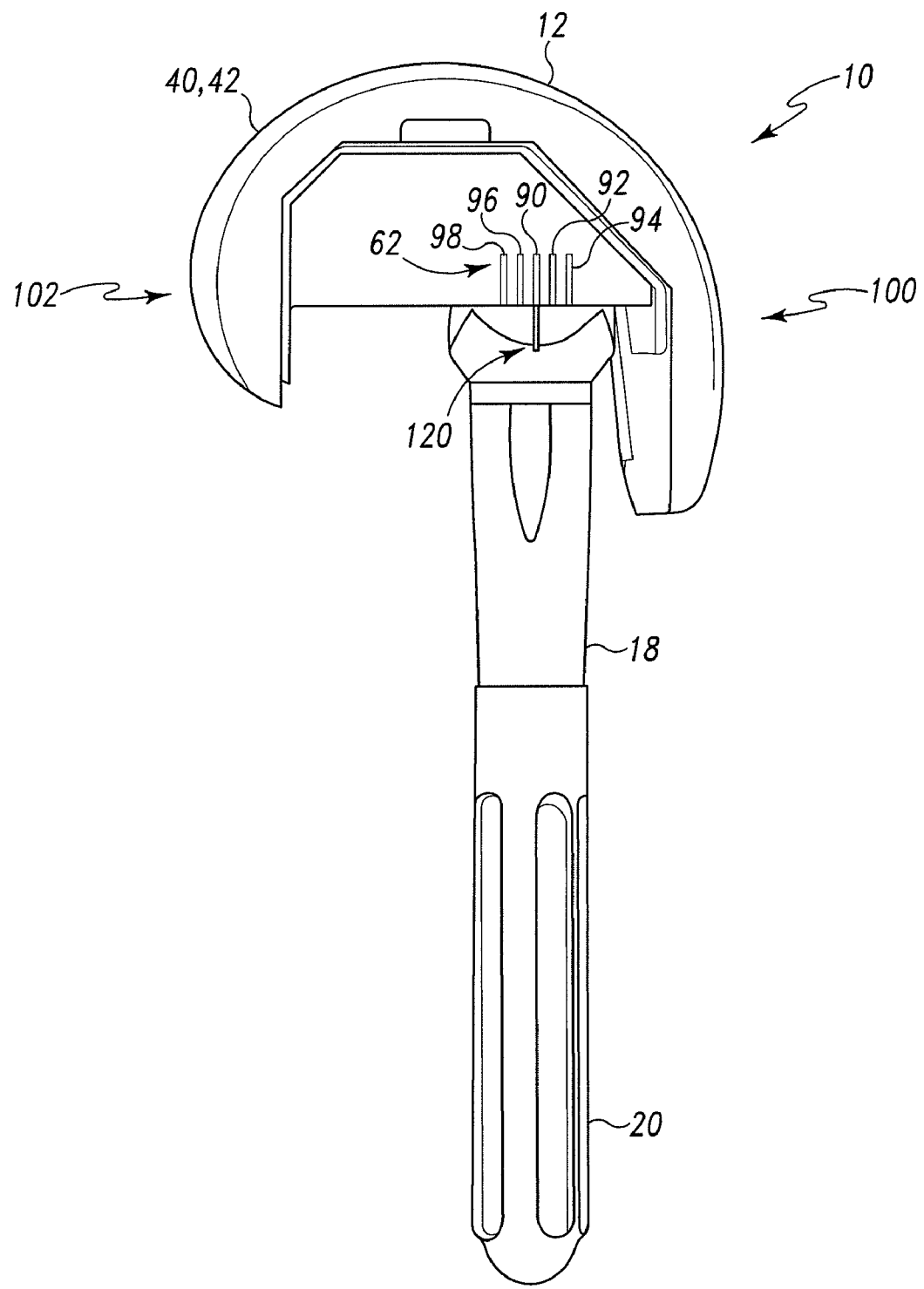
FIG. 9 is a side elevation view of one embodiment of the orthopaedic prosthesis of FIG. 1 in an assembled configuration including the plate of FIG. 5.

Once the plate 14 is coupled to the femoral component 10, the bolt 16 is inserted through the aperture 22 of the plate 14 and threaded into the threaded bore 36 of the stem 18 thereby securing the stem 18 to the femoral component 10. As discussed previously, the stem 18 may be secured to the femoral component 10 in one of a number of locations based on type of plate 14 used. That is, by selecting a plate 14 having the aperture 22 defined in a desired location, the position of the stem 18 may be adjusted. For example, if a plate 14 having the aperture 22 defined in a central location is used, such as the embodiment of plate 14 illustrated in and described above in regard to FIGS. 5-6, the stem 18 may be secured to the femoral component 10 in a central or no-offset location as illustrated in FIG. 9. In some embodiments, the stem 18 may include indicia 120 usable by the orthopaedic surgeon or other healthcare provider to determine the position of the stem 18 and, thereby, the aperture 22. That is, as illustrated in FIG. 9, when the stem 18 is coupled to the femoral component 10, the indicia 120 of the stem 18 corresponds to one of the indicia 62 of the femoral component 10. In the illustrative embodiment of FIG. 9, the indicia 120 of the stem 18 is aligned with the central or no-offset mark 90 of the femoral component 10, which indicates that the stem 18, and the aperture 22 are positioned in a central or no-offset location.

Figure 10:
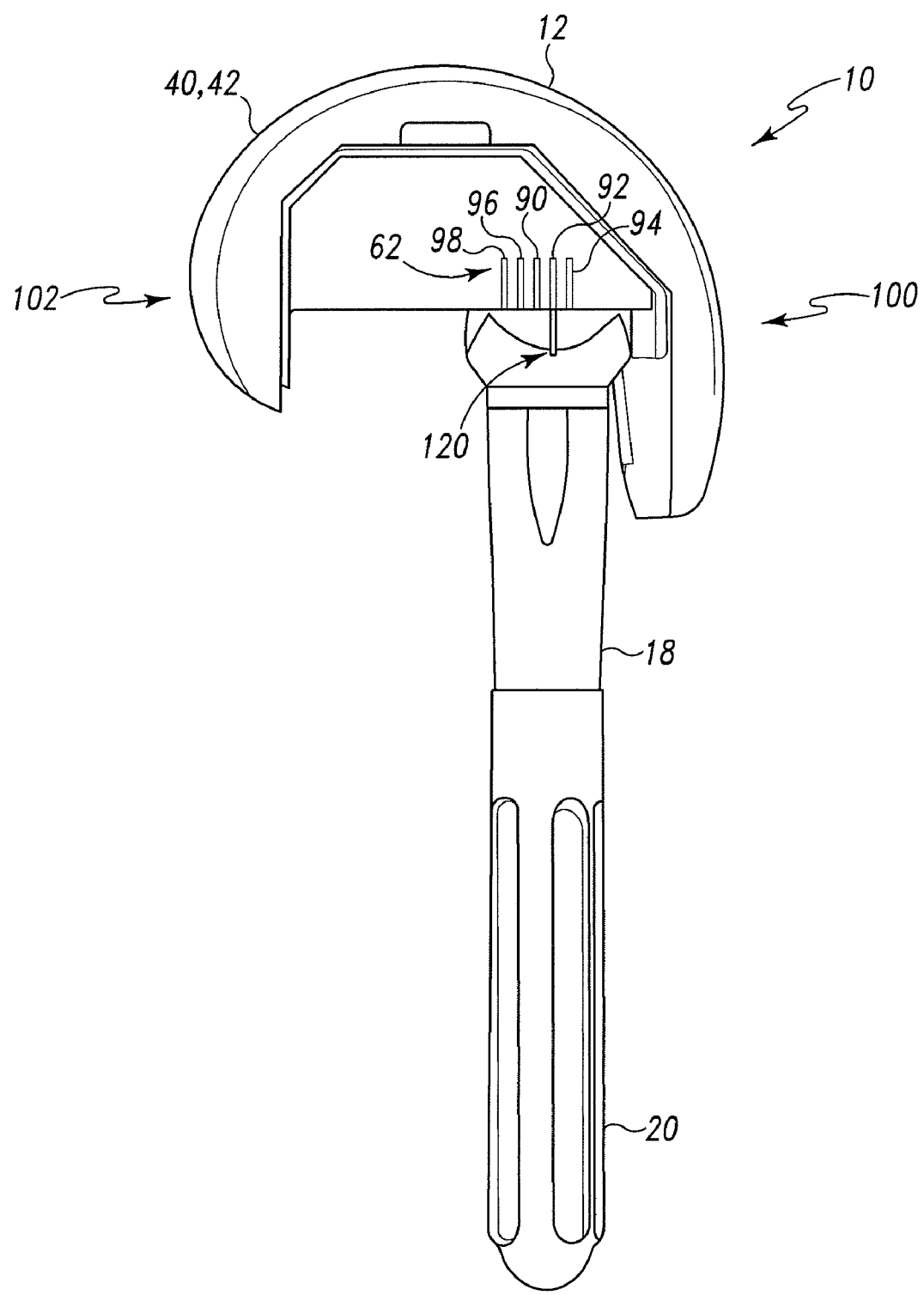
FIG. 10 is a side elevation view of another embodiment of the orthopaedic prosthesis of FIG. 1 in an assembled configuration including the plate of FIG. 7 positioned in a first orientation.
Figure 11:
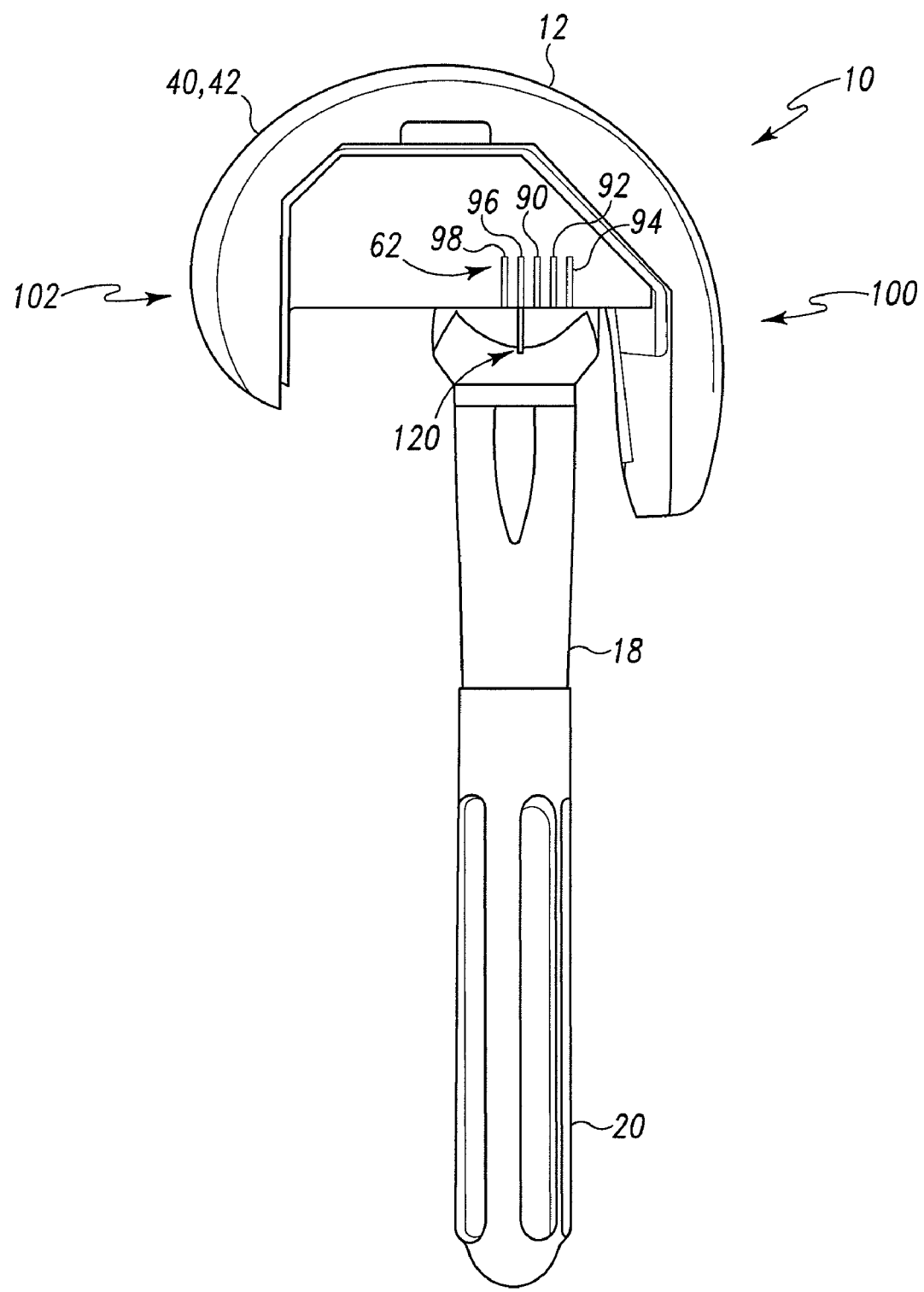
FIG. 11 is a side elevation view of the orthopaedic prosthesis of FIG. 10 having the plate of FIG. 7 positioned in a second orientation.
Figure 12:
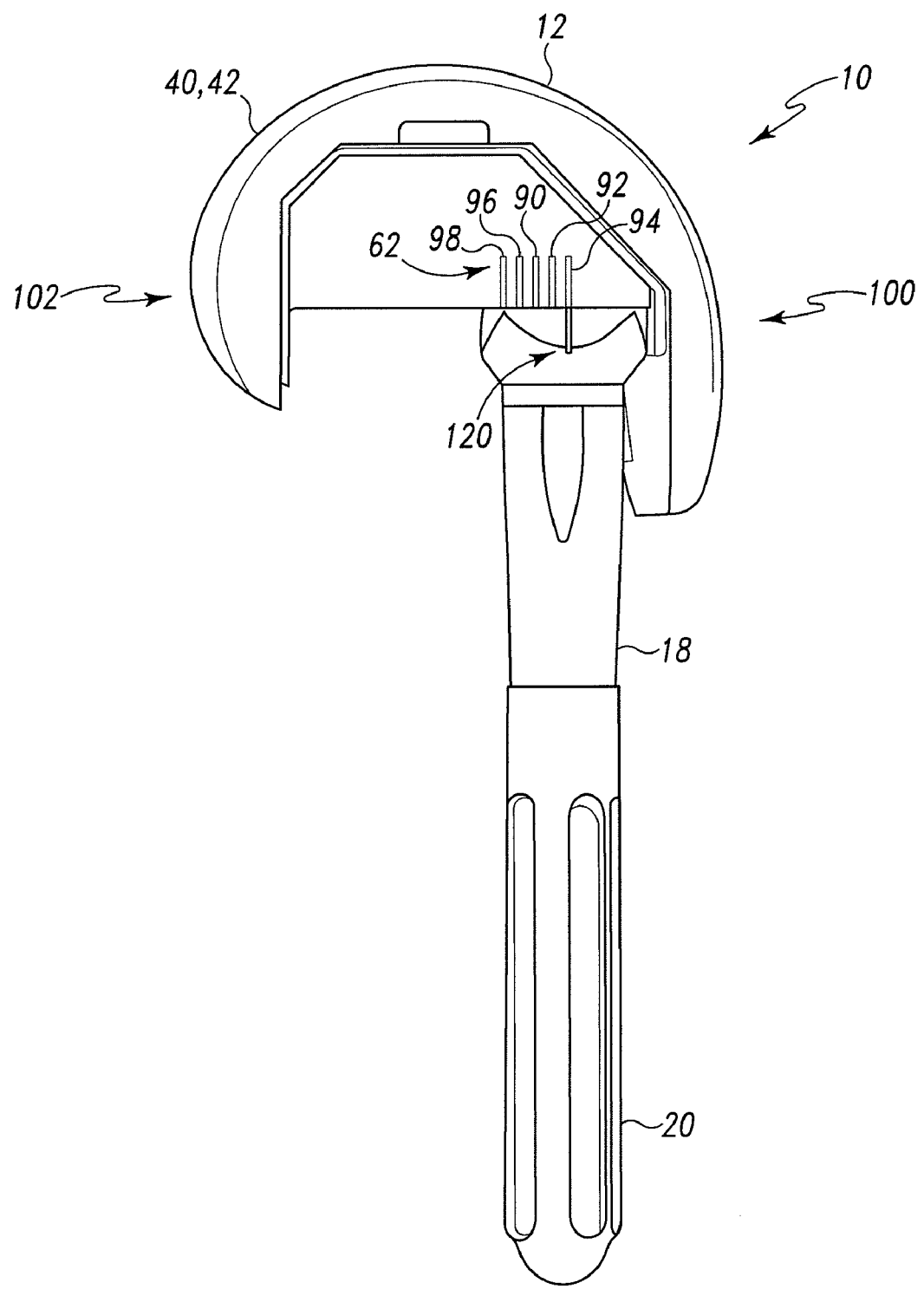
FIG. 12 is a side elevation view of another embodiment of the orthopaedic prosthesis of FIG. 1 in an assembled configuration including the plate of FIG. 8 positioned in a first orientation.
Figure 13:
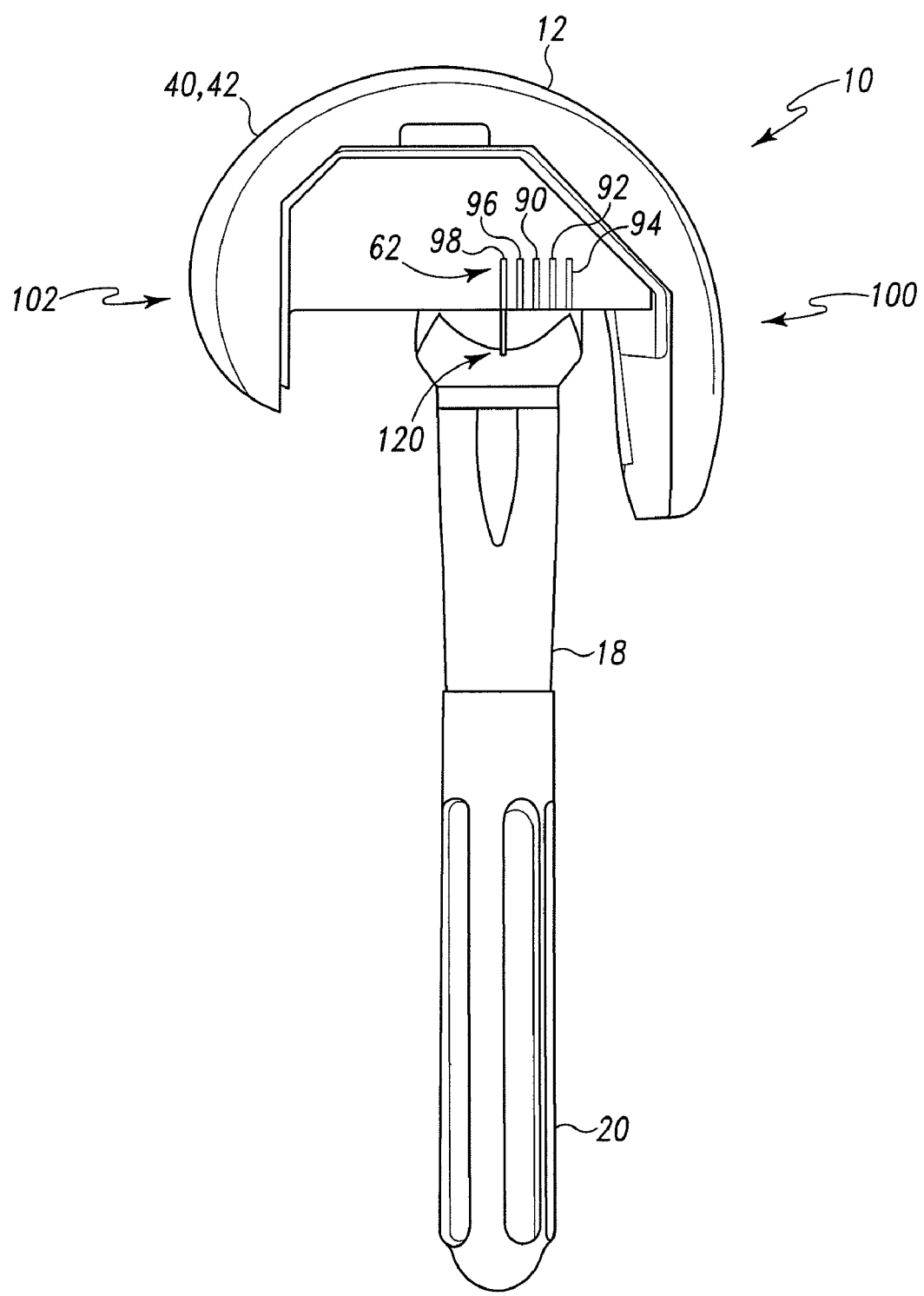
FIG. 13 is a side elevation view of the orthopaedic prosthesis of FIG. 12 having the plate of FIG. 8 positioned in a second orientation.

Alternatively, the stem 18 may be coupled to the femoral component 10 in an offset location via use of a plate 14 having the aperture 22 defined in a location offset from the center of the plate 14. For example, a plate 14 having the aperture 22 defined in an offset location similar the plate 14 illustrated in and described above in regard to FIGS. 7 and 8 may be used to secure the stem 18 to the femoral component 10 in an anterior or positive offset location as illustrated in FIGS. 10 and 12 or in a posterior or negative offset location as illustrated in FIGS. 11 and 13. That is, based on the orientation of the plate 14, the direction of offset of the stem 18 may be selected.

For example, the plate 14 may be coupled to the femoral component 10 such that the aperture 22 defined in the plate 14 is offset in the anterior direction. In such embodiments, the stem 18 may be secured to the femoral component 10 in an anterior offset location as illustrated in FIGS. 10 and 12. Alternatively, the plate 14 may be coupled to the femoral component 10 such that the aperture 22 defined in the plate 14 is offset in the posterior direction. In such embodiments, the stem 18 may be secured to the femoral component 10 in a posterior offset location as illustrated in FIGS. 11 and 13.

The amount of offset of the stem 18 is equal to the amount of offset of the aperture 22 from the center of the plate 14. For example, in the illustrative embodiments of FIGS. 10 and 11, the aperture 22 is defined in the plate 14 in a location offset from the center of the plate 14 by approximately two millimeters. As such, when the stem 18 is secured to the femoral component 10, the stem 18 is similarly offset from the neutral location by about two millimeters. Based on the orientation of the plate 14, the stem 18 may be offset by two millimeters in the anterior direction as illustrated in FIG. 10 or in the posterior direction as illustrated in FIG. 11. As illustrated in FIG. 10, when the stem 18 is offset in the anterior direction, the indicia 120 of the stem 18 is aligned with the first anterior or positive offset mark 92 of the femoral component 10, which indicates that the stem 18 and the aperture 22 are offset by two millimeters in the anterior direction. Alternatively, as illustrated in FIG. 11, when the stem 18 is offset in the posterior direction, the indicia 120 of the stem 18 is aligned with the first posterior or negative offset mark 96 of the femoral component 10, which indicates that the stem 18 and the aperture 22 are offset by two millimeters in the posterior direction.

Although the stem 18 is offset by two millimeters in the illustrative embodiment of FIGS. 10 and 11, the stem 18 may be offset by any amount in other embodiments. For example, in the illustrative embodiments of FIGS. 12 and 13, the aperture 22 is defined in the plate 14 in a location offset from the center of the plate 14 by approximately four millimeters similar to the embodiment of the plate 14 illustrated in and described above in regard to FIG. 8. As such, when the stem 18 is secured to the femoral component 10, the stem 18 is similarly offset by about four millimeters. Based on the orientation of the plate 14, the stem 18 may be offset by four millimeters in the anterior direction as illustrated in FIG. 12 or in the posterior direction as illustrated in FIG. 13. As illustrated in FIG. 10, when the stem 18 is offset in the anterior direction, the indicia 120 of the stem 18 is aligned with the second anterior or positive offset mark 94 of the femoral component 10, which indicates that the stem 18 and the aperture 22 are offset by four millimeters in the anterior direction. Alternatively, as illustrated in FIG. 13, when the stem 18 is offset in the posterior direction, the indicia 120 of the stem 18 is aligned with the second posterior or negative offset mark 98 of the femoral component 10, which indicates that the stem 18 and the aperture 22 are offset by four millimeters in the posterior direction.

It should be appreciated that the stem 18 may be coupled to the femoral component 10 in one of a number of locations based on the particular plate 14 used. Although in the illustrative embodiments, the stem 18 is offset by two or four millimeters, the stem 18 may be offset by one millimeter, three millimeters, or greater in other embodiments by use of a plate 14 having an aperture 22 defined in the appropriate location (i.e., defined at a corresponding offset location). As such, the stem 18 may be coupled to the femoral component in one of a number of locations based on the selection and orientation of the plate 14.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An orthopaedic prosthesis comprising:
   a femoral component configured to be coupled to a surgically-prepared surface of the distal end of a femur, the femoral component having a pair of spaced apart condyles and a planar surface extending between the pair of spaced apart condyles, the planar surface having an opening defined by a medial sidewall and a lateral sidewall, each of the medial and lateral sidewalls having a single slot defined therein extending downwardly from the planar surface and connected to the opening, and
   a plate including a body having (i) a pair of tabs extending outwardly therefrom, each of the tabs being configured to be received in a corresponding slot of the medial and lateral sidewalls when the plate is coupled to the femoral component and (ii) an aperture defined therethrough configured to receive a bolt,
   wherein the plate is configured to be coupled to the femoral component in one of a number of orientations such that (i) the aperture is in registry with the opening of the femoral component, (ii) the location of the aperture is adjustable relative to the femoral component based on the orientation of the plate, and (iii) a first tab of the pair of tabs is received in one of the single slots of the medial sidewall and the lateral sidewall in each of the number of orientations.

2. The orthopaedic prosthesis of claim 1, wherein the opening of the femoral component is further defined by an anterior sidewall, and a posterior sidewall.

3. The orthopaedic prosthesis of claim 1, wherein the aperture of the plate is longitudinally offset relative to the center of the plate.

4. The orthopaedic prosthesis of claim 3, wherein the aperture of the plate is longitudinally offset relative to the center of the plate by a distance of about 2 millimeters.

5. The orthopaedic prosthesis of claim 1, wherein the plate includes a flange defined on a distal side of the body, wherein the flange is placed in contact with the planar surface of the femoral component when the plate is coupled thereto.

6. The orthopaedic prosthesis of claim 1, wherein the plate is configured to be coupled to the femoral component in one of a first orientation and a second orientation, the plate being configured such that the aperture is (i) offset in an anterior direction relative to the center of the opening when the plate is in the first orientation and (ii) offset in a posterior direction relative to the center of the opening when the plate is in the second orientation.

7. The orthopaedic prosthesis of claim 1, wherein the femoral component includes indicia from which the location of the aperture may be determined.

8. The orthopaedic prosthesis of claim 1, further comprising:
   a stem having a threaded aperture; and
   a bolt, the bolt being configured to be inserted through the aperture of the plate and into the threaded aperture of the stem to secure the stem to the femoral component.

9. The orthopaedic prosthesis of claim 8, wherein the stem is configured to be coupled to the femoral component in one of a number of locations based on the orientation of the plate.

10. An orthopaedic prosthesis comprising:
    a femoral component configured to be coupled to a surgically-prepared surface of the distal end of a femur, the femoral component having (i) a planar surface, (ii) an opening for facilitating the attachment of a stem to the femoral component defined in the planar surface and positioned between a medial side and a lateral side of the femoral component, and (iii) a pair of slots defined in the planar surface and connected to the opening extending outwardly toward the medial side and the lateral side of the femoral component, respectively; and
    a plate having a body, a pair of tabs extending outwardly from the body, and a flange defined on a distal side of the body, the plate including an aperture defined therethrough, the plate being coupled to the femoral component in one of a number of orientations such that (i) the body of the plate is received in the opening, (ii) each of the pair of tabs is received in a corresponding slot of the pair of slots in each of the number of orientations, and (iii) the location of the aperture relative to the femoral component is adjustable based on the orientation of the plate.

11. The orthopaedic prosthesis of claim 10, wherein the opening of the femoral component is defined by an anterior sidewall, a posterior sidewall, a medial sidewall, and a lateral sidewall, each of the medial and lateral sidewalls having a slot defined therein.

12. The orthopaedic prosthesis of claim 10, wherein the flange of the plate is in contact with a distal surface of the femoral component.

13. The orthopaedic prosthesis of claim 10, wherein the aperture of the plate is longitudinally offset relative to the center of the plate.

14. The orthopaedic prosthesis of claim 10, the plate is configured to be coupled to the femoral component in one of a first orientation and a second orientation, the plate being configured such that the aperture is (i) offset in an anterior direction relative to the center of the opening when the plate is in the first orientation and (ii) offset in a posterior direction relative to the center of the opening when the plate is in the second orientation.

15. The orthopaedic prosthesis of claim 10, further comprising:
    a stem having a threaded aperture; and
    a bolt, the bolt being inserted through the aperture of the plate and into the threaded aperture of the stem thereby securing the stem to the femoral component in one of a number of locations based on the orientation of the plate.

16. The orthopaedic prosthesis of claim 15, wherein the femoral component and the stem include indicia from which the location of the aperture may be determined.

17. An orthopaedic prosthesis assembly comprising:
- a femoral component configured to be coupled to a surgically-prepared surface of the distal end of a femur, the femoral component having a pair of spaced apart condyles and a planar surface extending between the pair of spaced apart condyles, the planar surface having an opening defined by a medial sidewall and a lateral sidewall, each of the medial and lateral sidewalls having a single slot defined therein extending downwardly from the planar surface and connected to the opening;
- a plate having a body, a first tab extending outwardly from the body, a second tab extending outwardly from the body, and a flange defined on a distal side of the body, the plate including an aperture defined therethrough, the plate being configured to be coupled to the femoral component in a first orientation and a second orientation such that (i) the body of the plate is received in the opening, (ii) the aperture is offset in the anterior direction when the plate is in the first orientation, (iii) the aperture is offset in the posterior direction when the plate is in the second orientation, (iv) the first tab is received in the single slot of the medial sidewall and the second tab is received in the single slot of the lateral sidewall in the first orientation, and (v) the first tab is received in the single slot of the lateral sidewall and the second tab is received in the single slot of the medial sidewall in the second orientation;
- a stem having a threaded aperture; and
- a bolt, the bolt being configured to be inserted through the aperture of the plate and into the threaded aperture of the stem to secure the stem to the femoral component in one of a number of locations based on the orientation of the plate.

\* \* \* \* \*